United States Patent [19]

Nelson et al.

[11] Patent Number: 5,945,087
[45] Date of Patent: Aug. 31, 1999

[54] CYCLODEXTRINS IN DENTAL PRODUCTS

[75] Inventors: Dennis G. A. Nelson, Mountain Lake; Craig J. Sheehan, Edison, both of N.J.

[73] Assignee: Pfizer Inc., New York, N.Y.

[21] Appl. No.: 08/839,012

[22] Filed: Apr. 23, 1997

Related U.S. Application Data

[60] Provisional application No. 60/016,135, Apr. 24, 1996.
[51] Int. Cl.$^6$ ................ A61K 7/16; A61K 7/26
[52] U.S. Cl. ................ 424/49; 424/58
[58] Field of Search .................... 424/49–88

[56] References Cited

U.S. PATENT DOCUMENTS

| | | | |
|---|---|---|---|
| 4,267,166 | 5/1981 | Yajima | 424/48 |
| 4,727,064 | 2/1988 | Pitha | 514/58 |
| 5,095,035 | 3/1992 | Eby, III | 514/494 |
| 5,236,699 | 8/1993 | Libin | 424/54 |
| 5,310,546 | 5/1994 | Douglas | 424/523 |
| 5,356,615 | 10/1994 | Gaffar | 424/49 |
| 5,382,567 | 1/1995 | Fuwa et al. | 512/4 |
| 5,472,685 | 12/1995 | Gaffar | 424/49 |
| 5,626,837 | 5/1997 | Shimada et al. | 424/49 |
| 5,681,548 | 10/1997 | Esposito et al. | 424/49 |
| 5,723,106 | 3/1998 | Buch et al. | 424/49 |

FOREIGN PATENT DOCUMENTS 9416674  8/1994  WIPO .
9418939  9/1994  WIPO .

OTHER PUBLICATIONS

Chemical Abstrats 120:37785 of Shi CN 1071828A May 12, 1993 M mentholcyclodextrin.
Chemical Abstrats 124:15302 of Oshino et al JP 07238008A2 Sep. 12, 1995 M menthol cyclodextrin.
Chemical Abstrats 107:161426 Sato Sunstar JP 62116506A2 May 28, 1987 M menthol cyclodextrin toothpaste.
Chemical Abstrats 112:42263 Ootsuki Sunstar JP 01191623A2 Jul. 31, 1989 M menthol cyclodextrin mouthwash.
Chemical Abstrats 117:157445 Morishima Lion JP 04139118A2 May 13, 1992 T triclosgn cyclodextrin dentifrice.

*Primary Examiner*—Shep K. Rose
*Attorney, Agent, or Firm*—Peter C. Richardson; Paul H. Ginsburg; Grover F. Fuller, Jr.

[57] ABSTRACT

Oral rinse and dentifrice compositions, comprising a phenolic selected from the group consisting of menthol, eucalyptol, methyl salicylate, thymol, triclosan, and mixtures thereof; and a cyclodextrin selected from the group consisting of hydroxypropyl β-cyclodextrin, hydroxyethyl β-cyclodextrin, hydroxypropyl γ-cyclodextrin, hydroxyethyl γ-cyclodextrin, α-cyclodextrin, methyl β-cyclodextrin, and mixtures thereof. These compositions are useful in retarding the development of plaque, treating gingivitis, and in treating the presence of micro-organisms in the oral cavity.

15 Claims, No Drawings

CYCLODEXTRINS IN DENTAL PRODUCTS

This non-provisional application is based upon and claims priority from Provisional Application No. 60/016,135 filed Apr. 24, 1996.

BACKGROUND OF THE INVENTION

The present invention relates to dental products comprising cyclodextrins.

Dental plaque is present to some degree, in the form of a film, on virtually all dental surfaces. It is a by-product of microbial growth, and comprises a dense microbial layer consisting of a mass of micro-organisms embedded in a polysaccharide matrix. The micro-organisms present in plaque are mainly coccoidal organisms, particularly in early plaque. As plaque ages and matures, gram negative anaerobes and filamentous organisms appear and become more common after a few days. Plaque itself adheres to dental surfaces and may not be removed completely even with a rigorous brushing regimen and can build up, for example, in recessed areas of tooth surfaces, such as approximal regions and fissures. Moreover, plaque rapidly reforms on the tooth surface after it is removed.

Plaque may form on any part of the tooth surfaces, and can be found particularly at the gingival margin, in pits and fissures in the enamel, and on the surface of dental calculus. The danger associated with the formation of plaque on the teeth lies in the tendency of plaque to build up and eventually contribute to gingivitis, periodontitis and other types of periodontal disease, as well as dental caries and dental calculus.

More specifically, dental plaque is a precursor to the formation of the hard crystalline build up on teeth referred to as dental calculus. Both the bacterial and the nonbacterial components of plaque mineralize to form calculus, which comprises mineralized bacteria as well as organic constituents, such as epithelial cells, live bacteria, salivary proteins, leukocytes, and crystalline substances containing both calcium and phosphorous, e.g., hydroxyapatite, $Ca_{10}(PO_4)_6(OH)_2$, octacalcium phosphate, $Ca_8(HPO_4)_2(PO_4)_4 \cdot 5H_2O$, brushite, $CaHPO_4 \cdot 2H_2O$, and whitlockite, which is considered to have the formula $\beta\text{-}Ca_3(PO_4)_2$. Dental plaque and, hence, calculus are particularly prone to form at the gingival margin, i.e., the junction of the tooth and gingiva. The buildup of plaque at, and below, the gingival margin is believed to be the prime cause of gingivitis and periodontal disorders.

Mouthwashes have been formulated to contain antimicrobial ingredients whose function is to reduce the buildup of plaque, either by the direct bactericidal action (i.e. killing) on plaque and salivary micro-organisms and by bacteriostatic action (i.e. growth inhibition) on plaque and salivary micro-organisms. Scheie, A. AA. (1989) Modes of Action of Currently Known Chemical Anti-Plaque Agents Other than Chlorhexidine. J. Dent. Res. 68 Special Issue: 1609–1616. Oral compositions including mouthwashes and dentifrices containing phenolic compounds are referred to in U.S. Pat. Nos. 4,945,087; WO 94/16.16,674; WO 94/07477; and WO 94/18939. Oral composition including triclosan are referred to in the following: U.S. Pat. Nos. 4,892,220; 5,032,386; 5,037,637; 5,034,154; 5,080,887; 5,236,699; 5,043,154; 5,032,385; and 5,156,835 as well as EPO 85303216.7.

However phenolics useful in oral compositions have low aqueous solubilities which limit their use in oral compositions and they require high levels of either 1) alcohol; 2) surfactants; or 3) co-solvents or combinations of the above for sufficient solubility in the carrier. PCT Appln No. WO 94/16674.

For example, thymol has been used as a anthelmintic and antiseptic, in mouthwashes containing a combination of menthol, methyl salicylate, eucalyptol and thymol. However, these compositions are characterized by their relatively high alcohol levels which causes them to have negative aesthetics, including excessive "bite" and "burn."

Triclosan (2,4,4'-trichloro-2'-hydroxydiphenyl ether) is a phenolic, nonionic antimicrobial agent used in various soap and toiletry products. In the oral care area, triclosan has been used as a plaque-inhibitory agent in various toothpastes and mouthrinses. Triclosan is a broad-spectrum antimicrobial that has shown activity in in vitro assays. Regos, J. and Hitz, H. R. (1974) Investigation of Mode of Action of Triclosan, A Broad Spectrum Antimicrobial Agent. Zbl Bakt Hyg I Abt Orig A 226:390–401; Vischer, W. A. and Regos, J. (1974) Antimicrobial Spectrum of Triclosan, A Broad-Spectrum Antimicrobial Agent for Topical Application. Zbl Bakt Hyg I Agt Orig A 226:376–389, including chemostat studies; Bradshaw, D. J., Marsh, P. D., Watson, G. K. and Cummins, D. (1993) The Effects of Triclosan and Zinc Citrate, Alone and in Combination, on a Community of Oral Bacteria Grown in vitro. J. Dent Res. 72:25–30; Herles, S., Olsen, S., Afflito, J. and Gaffar, A. (1994) Chemostat Flow Cell System: An in vitro Model for the Evaluation of Antiplaque Agents. J. Dent Res. 73:1748–1755, as well as animal tests; Nabi, N., Mukerjee, C., Schmid, R., Gaffar, A. (1989) In Vitro and In Vivo Studies on Triclosan/PVM/MA copolymer/NaF Combination as an Antiplaque Agent. Am. J. Dent. Spec Issue No. 2:197–206; and human clinical studies; Garcia-Godoy, F., Garcia-Godoy, F., DeVizio, W., Volpe, A. R., Ferlauto, R. J. and Miller, J. M. (1990) Effect of a Triclosan/Copolymer/Fluoride Dentifrice on Plaque Formation and Gingivitis: A 7-month Clinical Study. Am. J. Dent. 3:S15–S26; Rustogi, K. N., Petrone, D. M., Singh, S. M., Volpe, A. R. and Tavss, E. (1990) Clinical Study of a Pre-brush and Triclosan/Copolymer Mouthrinse: Effect on Plaque Formation. Am. J. Dent. 3:S67–S69; and Saxton, C. A., Lane, R. M. and van der Ouderaa, F. (1987) The Effects of a Dentifrice Containing a Zinc Salt and a Non-cationic Antimicrobial Agent on Plaque and Gingivitis. J. Clin. Periodontol. 57:555–561. Although triclosan when delivered orally, is taken up by plaque and is moderately substantive, its bioactivity is limited by its poor aqueous solubility. Thus, triclosan has to be solubilized either by alcohol or surfactants such as sodium lauryl sulfate when formulated into a conventional dentifrice or mouthrinse product. Kjaerheim, V., Waaler, S. M., Rolla, G. (1994) Significance of Choice of Solvents for the Clinical Effect of Triclosan-containing Mouthrinses. Scand. J. Dent. Res. 102:202–205.

Cyclodextrins are known to form inclusion complexes with various compounds. The cyclodextrin molecule consists of glucopyranose units arranged in a torus-like or donut-like configuration having all the secondary hydroxyl groups located on one side of the torus and all primary hydroxyl groups located on the other side. Alpha, beta, and gamma cyclodextrin contain 6, 7 & 8 cyclic glucopyranose units, respectively, in the torus shell. The "lining" of the internal cavity is formed by hydrogen and glucosidic oxygen-bridge atoms and therefore the surface is slightly apolar.

SUMMARY OF THE INVENTION

The present invention relates to an oral rinse composition, comprising:

a) from about 0.01% to about 2.5% by weight of a phenolic, said phenolic selected from the group consisting of menthol, eucalyptol, methyl salicylate, thymol, triclosan, and mixtures thereof;

b) From about 0.1% by weight to about 25% by weight of a cyclodextrin, said cyclodextrin selected from the group consisting of hydroxypropyl β-cyclodextrin, hydroxyethyl β-cyclodextrin, hydroxypropyl γ-cyclodextrin, hydroxyethyl γ-cyclodextrin, α-cyclodextrin, methyl β-cyclodextrin, and mixtures thereof;

c) Up to about 25% by weight ethanol; and d) an orally acceptable carrier.

The present invention also relates to a dentifrice in the form of a toothpaste or tooth gel, comprising:

a) from about 0.01% to about 10% by weight of a phenolic, said phenolic selected from the group consisting of menthol, eucalyptol, methyl salicylate, thymol, triclosan, and mixtures thereof;

b) From about 0.1% by weight to about 60% by weight of a cyclodextrin, said cyclodextrin selected from the group consisting of hydroxypropyl β-cyclodextrin, hydroxyethyl β-cyclodextrin, hydroxypropyl γ-cyclodextrin, hydroxyethyl γ-cyclodextrin, α-cyclodextrin, methyl β-cyclodextrin, and mixtures thereof;

c) up to about 60% by weight of an orally acceptable dental abrasive, for example, silica, alumina, calcium pyrophosphate and calcium carbonate; and d) an orally acceptable carrier.

The present also relates to a method for retarding development of plaque on a dental surface in the oral cavity of a mammal, comprising administering to said dental surface an amount of said oral rinse composition effective in retarding said development of plaque.

The present also relates to a method for retarding development of plaque on a dental surface in the oral cavity of a mammal, comprising administering to said dental surface an amount of said dentifrice effective in retarding said development of plaque.

The present also relates to a method of treating gingivitis, comprising administering to a mammal in need of such treatment an amount of said oral rinse composition effective in treating gingivitis.

The present also relates to a method of treating gingivitis, comprising administering to a mammal in need of such treatment an amount of said dentifrice effective in treating gingivitis.

The present also relates to a method of treating the presence of micro-organisms in the oral cavity of a mammal, comprising administering to the mammal in need of such treatment an amount of said oral rinse composition effective in reducing the viable population of said micro-organisms.

The present also relates to a method of treating the presence of micro-organisms in the oral cavity of a mammal, comprising administering to the mammal in need of such treatment an amount of said dentifrice effective in reducing the viable population of said micro-organisms.

DETAINED DESCRIPTION OF THE INVENTION

Compositions of the present invention include low-alcohol oral care compositions that contain cyclodextrin compounds which solubilize phenolic antimicrobial compounds. As a result of higher levels of solubilized phenolics in a solution, the phenolic compounds have improved bioavailability in treating plaque, as well as providing compositions having excellent low-temperature stability. These compositions retard the development of plaque as well as treat gingivitis and periodontal diseases without the use of high alcohol levels, high surfactant levels or the use of other co-solvents.

Phenolics useful as antimicrobials in the present invention and effective in treating micro-organisms present in the oral cavity of a mammal include menthol, methyl salicylate, eucalyptol, thymol and triclosan. Thymol and triclosan are generally considered to have the best antimicrobial activity of these phenolics. For oral rinses, phenolic compounds or mixtures thereof preferably range from about 0.01% by weight to about 0.5% by weight, more preferably from about 0.05% by weight to about 0.3% by weight. For dentifrices, the amount of phenolic compounds or a mixture thereof preferably range from about 0.01% by weight to about 5% by weight, more preferably from about 0.25% by weight to about 3% by weight.

Molecules, or functional groups of molecules having molecular dimensions that match the cyclodextrin cavity, being less hydrophilic (i.e. more hydrophobic) than water, will position themselves in the cyclodextrin cavity at the expense of water molecules. In aqueous solutions, the slightly apolar cyclodextrin cavity is occupied by water molecules which are energetically unfavored (polar-apolar interaction) and are therefore readily substituted by appropriate "guest molecules" which are less polar than water. In the case of the present invention, the "guest molecules" are the phenolic ingredients mentioned above.

Suitable cyclodextrins useful in the present invention include hydroxypropyl β-cyclodextrin, hydroxyethyl β-cyclodextrin, hydroxypropyl γ-cyclodextrin, hydroxyethyl γ-cyclodextrin, α-cyclodextrin and methyl β-cyclodextrin. Suitable candidate cyclodextrins typically have to have an aqueous solubility of at least about 10% by weight and form sufficiently soluble phenolic-cyclodextrin complexes to be suitable for this invention. Hydroxypropyl β-cyclodextrin is the preferred cyclodextrin.

Each of the seven cyclic glucopyranose units in β-cyclodextrin contains three hydroxyl groups in the 2-,3- and 6-positions, which can be etherified. In the case of the partially etherified cyclodextrin derivatives used in this invention, only some of these positions are substituted with hydroxyethyl or hydroxypropyl groups. A wide range of substitutions can be made per molecule up to a maximum of 18. The preferred range of substitution ranges from about 0.5 to 8 positions. Thus, hydroxypropyl β-cyclodextrin is a chemically modified cyclodextrin consisting of an amorphous isomeric mixture of thousands of geometric and optical isomers with varying degrees of substitution and varying numbers of hydroxypropyl substituents, however the size of the cyclodextrin cavity is constant for these isomers.

For oral rinses, these amount of soluble cyclodextrin ranges from about 0.1% by weight to about 25% by weight, preferably from about 0.5% by weight to about 20% by weight, more preferably from about 1% by weight to about 5% by weight, selected from the group consisting of hydroxypropyl β-cyclodextrin, hydroxyethyl β-cyclodextrin, hydroxypropyl γ-cyclodextrin, hydroxyethyl β-cyclodextrin, α-cyclodextrin, methyl β-cyclodextrin, and mixtures thereof are useful for the invention. For dentifrices, the amount of soluble cyclodextrin ranges from about 0.1% by weight to about 60% by weight, preferably from about 5% by weight to about 30% by weight selected from the group consisting of hydroxypropyl β-cyclodextrin, hydroxyethyl β-cyclodextrin, hydroxypropyl γ-cyclodextrin, hydroxyethyl γ-cyclodextrin, α-cyclodextrin, methyl β-cyclodextrin, and mixtures thereof are useful for the invention.

For dentifrice compositions suitable abrasives include precipitated silica or silica gels which have an average particle size ranging from about 0.1 to about 50 microns. Preferred silica abrasives include those marketed under the tradename "Sylodent®" or "Syloid®" by the W. R. Grace & Co. and those marketed under the tradename "Zeodent®" by the J. M. Huber Corp. Other suitable abrasives, having a suitable particle size as described above, include β-phase calcium pyrophosphate, alumina and calcium carbonate. The amount of abrasive in a dentifrice composition ranges up to about 60% by weight, preferably from 10% by weight to 40% by weight.

Dentifrice and oral rinse compositions also may contain a suitable fluoride source. Typical sources include soluble salts of the fluoride ion; e.g. sodium fluoride, potassium fluoride, stannous fluoride, stannous fluorozirconate etc.; or, soluble salts of the monofluorophosphate ion; e.g. sodium monofluorophosphate etc. The preferred fluoride source is sodium fluoride. The fluoride ion source should be sufficient to provide from about 50 ppm to about 2,500 ppm fluoride, preferably from about 250 ppm to about 1500 ppm for dentifrices and from about 50 ppm to about 250 ppm fluoride for oral rinses.

A liquid carrier generally includes mixtures of water and ethanol for oral rinses, although the carrier can be alcohol-free, especially in dentifrices. For oral rinses, the amount of water ranges upwards from about 25% by weight. The amount of alcohol ranges by weight from about 0% to about 25% by weight, preferably from about 0% by weight to about 15% by weight. For dentifrices, the amount of water ranges from about 0% by weight to about 60% by weight, preferably from about 0% by weight to about 40% by weight.

The pH of the oral rinses and dentifrice compositions can range from about 3.5 to about 8.5.

The oral rinse compositions, for example, Examples 1 to 5, are unusually stable so as to be substantially clear and substantially free of precipitation, flocculation, or crystal formation at about room temperature (about 25° C.) as well as at low temperatures of at least about 5° C. for at least about 1 week. The low temperature stability of these compositions is determined by cooling the compositions to about 5° C., storing for at least seven days and determining whether any precipitate, crystallized or flocculated material is formed in the clear compositions (solutions and gels).

Oral surfactants useful in the present invention include nonionic and anionic surfactants. Oral surfactants employed include block co-polymers of polyoxyethylene and polyoxypropylene such as the Pluronics from BASF. Other oral surfactants include soluble alkyl sulfonates having 10 to 18 carbon atoms, such as sodium lauryl sulfate, and sulfates of monoglycerides of fatty acids having 10 to 18 carbon atoms or sarcosinates (including salts and derivatives) such as sodium-N-lauroyl sarcosinate. Mixtures of anionic and nonionic surfactants can be used. These ingredients are generally present from about 0% by weight to about 4% by weight, preferably from about 0% by weight to about 1% by weight for oral rinses and from about 0.5% by weight to about 4% by weight for dentifrices.

Additional antiplaque agents can also be optionally added to the compositions. These include cetyl pyridinium chloride and related quaternary salts, chlorhexidine, zinc salts such as zinc chloride, stannous salts such as stannous chloride or stannous fluoride and peroxygens such as hydrogen peroxide and carbamide peroxide. These optional antiplaque agents are generally present at levels ranging form about 0% to about 5% by weight.

Additional anticalculus agents can be optionally added to the compositions. These include tetra-alkali or di-alkali metal pyrophosphate salts and zinc salts, such as, but not limited to, zinc chloride etc. These optional anticalculus agents are generally present at levels ranging from about 0% by weight to about 10% by weight for pyrophosphate salts and from about 0% by weight to about 3% by weight for zinc salts.

In compositions relating to the invention, preservatives may be used, especially for non-alcohol or low alcohol compositions. These include benzoic acid, sodium benzoate, methylparaben, propylparaben, sorbic acid and potassium sorbate. These optional preservative agents are generally present at levels ranging from about 0% by weight to about 2% by weight.

In compositions relating to the invention, buffering systems may be used to stabilize the pH in the product. Typical buffering systems include, but are not limited to, citrate, benzoate, gluconate and phosphate. Buffering systems are present in concentrations from about 0.01% by weight to about 1% by weight.

In addition to the above ingredients, the invention may include other optional ingredients to impart desired mouth feel and provide flavoring and coloring.

Humectants are an optional component of the compositions. For oral rinses they impart a moist and elegant feel to the mouth and in toothpaste compositions they prevent hardening on exposure to air. Some humectants can provide sweetness to the composition. Suitable humectants include edible polyhydric alcohols such as glycerin, sorbitol, propylene glycol and xylitol. The humectant generally is present in an amount ranging from 0% by weight to 30% by weight for oral rinses and 0% by weight to 70% by weight for dentifrice compositions.

Thickening agents or binders are an optional component of the compositions. Typical thickening include, xanthan gum, carrageenan, carboxyvinyl polymers, carbomers, cellulose gums such as carboxymethyl cellulose, cellulose derivatives such as hydroxyethylcellulose and silicas. Thickeners are usually present in the compositions from about 0% by weight to 2% by weight. Xanthan gum is the preferred thickener in oral rinses. In dentifrices, silica-based thickeners can be used at concentrations from 0% by weight to about 20% by weight. "Sylox®" by W. R. Grace & Co. is the tradename of the preferred silica-based thickener.

Flavoring agents can be added to the compositions. The flavorant may be a flavoring oil or mixture of flavoring oils such as oil of peppermint, spearmint, wintergreen, clove, sassafras, lemon, orange or lime. Sweetening agents such as saccharin, lactose, maltose, aspartame, sodium cyclamate, polydextrose etc. can be added to the compositions. Flavoring agents generally are present in an amount ranging from 0.001% by weight to about 0.5% by weight for oral rinses and 0.25% by weight to about 5% by weight for dentifrice compositions. Sweetening agents generally are present in an amount ranging from 0.001% by weight to about 5% by weight for oral rinse and dentifrice compositions. Coloring agents generally are present in an amount ranging from 0% by weight to 0.01% by weight.

EXAMPLE 1

A dental rinse was formulated by adding Hydroxypropyl β-cyclodextrin and poloxamer to water using a Master Servodyne® mixer with high-lift blade rotating at 200–300 rpm to give a clear aqueous solution. Benzoic acid, thymol, menthol, eucalyptol, methyl salicylate and flavor were added with stirring to give a clear solution. Sodium citrate, citric acid, dye, sorbitol and sodium saccharin were then added with continual stirring to give a clear solution. The resulting clear blue-green product was mixed for a further 30 minutes. The product had a pH of approximately 4.0.

| Ingredient | Weight Percent |
| --- | --- |
| poloxamer 407 | 0.50 |
| sodium citrate | 0.04 |
| citric acid | 0.01 |
| sorbitol 70% | 22.00 |
| FD + C green no. 3 | 0.0006 |
| hydroxypropyl β-cyclodextrin | 5.00 |
| sodium saccharin | 0.05 |
| benzoic acid | 0.15 |
| thymol | 0.064 |
| eucalyptol | 0.092 |
| menthol | 0.042 |
| methyl salicylate | 0.060 |
| flavor | 0.10 |
| purified water | 71.8914 |
| total | 100.0000 |

EXAMPLE 2

A dental rinse was formulated by adding poloxamer, sodium citrate, citric acid, sodium saccharin, hydroxypropyl β-cyclodextrin, sorbitol and dye to water, at room temperature, using a Master Servodyne® mixer with high-lift blade rotating at 200–300 rpm to give a clear aqueous solution. Benzoic acid, menthol, thymol, methyl salicylate, eucalyptol and flavor were added to the 190° alcohol to give a clear alcoholic solution. The alcoholic phase was added slowly to the aqueous phase which was continually agitated until the addition was complete. The resulting clear blue-green product was mixed for a further 30 minutes. The product had a pH of approximately 4.0.

| Ingredient | Weight Percent |
| --- | --- |
| poloxamer 407 | 0.50 |
| sodium citrate | 0.04 |
| citric acid | 0.01 |
| sorbitol 70% | 22.00 |
| FD + C green no. 3 | 0.0006 |
| hydroxypropyl β-cyclodextrin | 1.0 |
| sodium saccharin | 0.05 |
| alcohol 190 proof | 12.00 |
| benzoic acid | 0.15 |
| thymol | 0.064 |
| eucalyptol | 0.092 |
| menthol | 0.042 |
| methyl salicylate | 0.060 |
| flavor | 0.10 |
| purified water | 63.8914 |
| total | 100.0000 |

EXAMPLE 3

A dental rinse was formulated by adding poloxamer, sodium citrate, citric acid, sodium saccharin, hydroxypropyl β-cyclodextrin, sorbitol and dye to water using a Master Servodyne® mixer with high-lift blade rotating at 200–300 rpm to give a clear aqueous solution. Benzoic acid, triclosan (Irgacare MP—Ciba Geigy) and flavor were added to the 190° alcohol to give a clear alcoholic solution. The alcoholic phase was added slowly to the aqueous phase which was continually agitated until the addition was complete. The resulting clear blue-green product was mixed for a further 30 minutes. The product had a pH of approximately 4.0.

| Ingredient | Weight Percent |
| --- | --- |
| poloxamer 407 | 0.50 |
| sodium citrate | 0.04 |
| citric acid | 0.01 |
| sorbitol 70% | 22.00 |
| FD + C green no. 3 | 0.0006 |
| hydroxypropyl β-cyclodextrin | 2.50 |
| sodium saccharin | 0.05 |
| alcohol 190 proof | 8.00 |
| benzoic acid | 0.15 |
| triclosan | 0.10 |
| flavor | 0.10 |
| purified water | 66.5494 |
| total | 100.0000 |

EXAMPLE 4

A dental rinse was formulated by adding poloxamer, sodium citrate, citric acid, sodium saccharin, hydroxypropyl β-cyclodextrin, sorbitol and dye to water, at room temperature, using a Master Servodyne® mixer with high-lift blade rotating at 200–300 rpm to give a clear aqueous solution. Benzoic acid, menthol, thymol, methyl salicylate, eucalyptol and flavor were added to the 190° alcohol to give a clear alcoholic solution. The alcoholic phase was added slowly to the aqueous phase which was continually agitated until the addition was complete. The resulting clear blue-green product was mixed for a further 30 minutes. The product had a pH of approximately 4.0.

| Ingredient | Weight Percent |
| --- | --- |
| poloxamer 407 | 0.50 |
| sodium citrate | 0.04 |
| citric acid | 0.01 |
| sorbitol 70% | 22.00 |
| FD + C green no. 3 | 0.0006 |
| hydroxypropyl β-cyclodextrin | 1.25 |
| sodium saccharin | 0.05 |
| alcohol 190 proof | 8.00 |
| benzoic acid | 0.15 |
| thymol | 0.064 |
| eucalyptol | 0.092 |
| menthol | 0.042 |
| methyl salicylate | 0.060 |
| flavor | 0.10 |
| purified water | 67.6414 |
| total | 100.0000 |

EXAMPLE 5

A dental rinse was formulated by adding poloxamer, sodium citrate, citric acid, sodium saccharin, hydroxypropyl β-cyclodextrin, zinc chloride, sorbitol and dye to water using a Master Servodyne® mixer with high-lift blade rotating at 200–300 rpm to give a clear aqueous solution. Benzoic acid, menthol, thymol, methyl salicylate, eucalyptol and flavor were added to the 190° alcohol to give a clear alcoholic solution. The alcoholic phase was added slowly to the aqueous phase which was continually agitated until the addition was complete. The resulting clear blue-green product was mixed for a further 30 minutes. The product had a pH of approximately 4.0.

| Ingredient | Weight Percent |
| --- | --- |
| poloxamer 407 | 0.50 |
| sodium citrate | 0.04 |
| citric acid | 0.01 |
| sorbitol 70% | 22.00 |
| FD + C green no. 3 | 0.0006 |
| hydroxypropyl β-cyclodextrin | 1.25 |
| zinc chloride | 0.10 |
| sodium saccharin | 0.03 |
| alcohol 190 proof | 8.00 |
| benzoic acid | 0.15 |
| thymol | 0.064 |
| eucalyptol | 0.092 |
| menthol | 0.042 |
| methyl salicylate | 0.060 |
| flavor | 0.10 |
| purified water | 67.5614 |
| total | 100.0000 |

EXAMPLE 6

A gel dentifrice was formulated by dispersing carboxymethyl cellulose in the glycerin and polyethylene glycol using a Lightening mixer. NaF was dissolved separately in the water. Water and sorbitol were added and mixed for 25 minutes sodium saccharin and hydroxypropyl β-cyclodextrin were then added and mixed for a further 10 minutes. The phenolics were mixed together, i.e. eucalyptol, methyl salicylate, thymol and menthol, to make a phenolic phase. The phenolic phase was added to the cellulose/sorbitol/cyclodextrin/water phase until the phenolics are dissolved. Sylodent® 700, Sylox® 2, FD+C Blue No. 1 and sodium lauryl sulfate were then added and mixed thoroughly for 30 minutes. The resulting clear blue gel was deaerated to remove air bubbles.

| Ingredient | Weight Percent |
| --- | --- |
| glycerin | 14.000 |
| sorbitol, 70% | 27.343 |
| carboxymethyl cellulose, 9M8 | 0.900 |
| polyethylene glycol, PEG-8 | 3.000 |
| purified water | 13.429 |
| FD + C blue no. 1 | 0.005 |
| hydroxypropyl β-cyclodextrin | 15.000 |
| sodium saccharin | 0.500 |
| NaF | 0.243 |
| Sylodent ® 700 | 14.000 |
| Sylox ® 2 | 8.000 |
| thymol | 0.640 |
| eucalyptol | 0.920 |
| menthol | 0.420 |
| methyl salicylate | 0.600 |
| sodium lauryl sulfate | 1.000 |

We claim:
1. A stable oral rinse composition, comprising:
a) from about 0.01% to about 2.5% by weight of a phenolic, said phenolic selected from the group consisting of (i) a combination of menthol, eucalyptol, methyl salicylate, and thymol, (ii) triclosan, and (iii) mixtures thereof;
b) from about 0.1% by weight to about 25% by weight of a soluble cyclodextrin capable of solubilizing said phenolic without the use of high alcohol levels, high surfactant levels, or other phenolic consolvents, said soluble cyclodextrin selected from the group consisting of hydroxypropyl β-cyclodextrin, hydroxyethyl β-cyclodextrin, hydroxypropyl γ-cyclodextrin, hydroxyethyl γ-cyclodextrin, α-cyclodextrin, methyl β-cyclodextrin, and mixtures thereof,
c) up to about 25% by weight ethanol; and
d) an orally acceptable carrier
said composition being low temperature stable and substantially clear and substantially free of precipitants, flocculants, or crystals at about room temperature.
2. A stable oral rinse composition according to claim 1, wherein the amount of cyclodextrin is from about 1% by weight to about 5% by weight.
3. A stable oral rinse composition according to claim 1, wherein the amount of ethanol is up to about 15% by weight.
4. A stable oral rinse composition according to claim 1, further including up to about 4% by weight of an orally acceptable surfactant selected from the group consisting of an anionic surfactant, a nonionic surfactant, or mixtures thereof.
5. A stable oral rinse composition according to claim 4, wherein the amount of orally acceptable surfactant is up to about 1% by weight.
6. A stable oral rinse composition according to claim 1, further including up to about 5% by weight of an orally acceptable antiplaque agent.
7. A stable oral rinse composition according to claim 6, wherein the orally acceptable antiplaque agent is selected from the group consisting of cetyl pyridinium chloride, cetyl pyridinium chloride related quaternary pharmaceutically acceptable salts, chlorhexidine, zinc pharmaceutically acceptable salts, stannous pharmaceutically acceptable salts and pharmaceutically acceptable peroxygens.
8. A stable oral rinse composition according to claim 1, further including an orally acceptable anticalculus agent.
9. A stable oral rinse composition according to claim 8, wherein the orally acceptable anticalculus agent includes up to about 10% by weight of a pyrophosphate pharmaceutically acceptable salt.
10. A stable oral rinse composition according to claim 1, further including an orally acceptable suitable fluoride ion source sufficient to provide from about 50 ppm to about 2500 ppm fluoride.
11. A stable oral rinse composition according to claim 10, wherein the amount of the orally acceptable suitable fluoride ion source provides from about 50 ppm to about 250 ppm fluoride.
12. A stable oral rinse composition, comprising:
a) from about 0.01% to about 0.5% by weight of a phenolic, said phenolic selected from the group consisting of (i) a combination of menthol, eucalyptol, methyl salicylate, and thymol, (ii) triclosan, and (iii) mixtures thereof;
b) from about 0.1% by weight to about 5% by weight of a cyclodextrin capable of solubilizing said phenolic without the use of high alcohol levels, high surfactant levels, or other phenolic cosolvents, said soluble cyclodextrin selected from the group consisting of hydroxypropyl β-cyclodextrin, hydroxyethyl β-cyclodextrin, hydroxypropyl γ-cyclodextrin, hydroxyethyl γ-cyclodextrin, α-cyclodextrin, methyl β-cyclodextrin, and mixtures thereof;
c) up to about 15% by weight ethanol; and
d) up to about 1% by weight of an orally acceptable surfactant selected from the group consisting of an anionic surfactant, a nonionic surfactant, or mixtures thereof; and d) an orally acceptable carrier said composition being low temperature stable and substantially clear and substantially free of precipitants, flocculants, or crystals at about room temperature.

13. A method for retarding development of plaque on a dental surface in the oral cavity of a mammal, comprising administering to said dental surface an amount of a composition according to claim 1 effective in retarding said development of plaque.

14. A method of treating gingivitis, comprising administering to a mammal in need of such treatment an amount of a composition according to claim 1 effective in treating gingivitis.

15. A method of treating the presence of micro-organisms in the oral cavity of a mammal, comprising administering to the mammal in need of such treatment an amount of a composition according to claim 1 effective in reducing the viable population of said micro-organisms.

* * * * *